US009629563B2

United States Patent
Sharma et al.

(10) Patent No.: US 9,629,563 B2
(45) Date of Patent: Apr. 25, 2017

(54) METHOD AND SYSTEM FOR FUNCTIONAL ASSESSMENT OF RENAL ARTERY STENOSIS FROM MEDICAL IMAGES

(71) Applicants: Puneet Sharma, Monmouth Junction, NJ (US); Saikiran Rapaka, Ewing, NJ (US); Viorel Mihalef, North Brunswick, NJ (US); Ali Kamen, Skillman, NJ (US)

(72) Inventors: Puneet Sharma, Monmouth Junction, NJ (US); Saikiran Rapaka, Ewing, NJ (US); Viorel Mihalef, North Brunswick, NJ (US); Ali Kamen, Skillman, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 379 days.

(21) Appl. No.: 14/477,770

(22) Filed: Sep. 4, 2014

(65) Prior Publication Data
US 2015/0065864 A1     Mar. 5, 2015

Related U.S. Application Data

(60) Provisional application No. 61/873,399, filed on Sep. 4, 2013, provisional application No. 61/891,920, filed on Oct. 17, 2013.

(51) Int. Cl.
*A61B 5/026*     (2006.01)
*A61B 5/021*     (2006.01)
(Continued)

(52) U.S. Cl.
CPC ............ *A61B 5/0263* (2013.01); *A61B 5/021* (2013.01); *A61B 5/055* (2013.01);
(Continued)

(58) Field of Classification Search
CPC . A61B 5/0263; A61B 5/055; A61B 2576/023; A61B 5/021; G01R 33/5635; G01R 33/56316
See application file for complete search history.

(56) References Cited

U.S. PATENT DOCUMENTS

| 7,953,266 B2 | 5/2011 | Gulsun et al. |
| 8,098,918 B2 | 1/2012 | Zheng et al. |

(Continued)

FOREIGN PATENT DOCUMENTS

WO     2013138428 A1     9/2013

OTHER PUBLICATIONS

Taylor, "Open Problems in Computational Vascular Biomechanics: Hemodynamics and Arterial Wall Mechanics," Comput Methods Appl Mech Eng, vol. 198, pp. 3514-3523, 2009.

(Continued)

*Primary Examiner* — Bo J Peng (57) ABSTRACT

A method and system for non-invasive assessment of renal artery stenosis is disclosed. A patient-specific anatomical model of at least a portion of the renal arteries and aorta is generated from medical image data of a patient. Patient-specific boundary conditions of a computational model of blood flow in the portion of the renal arteries and aorta are estimated based on the patient-specific anatomical model. Blood flow and pressure are simulated in the portion of the renal arteries and aorta using the computational model based on the patient-specific boundary conditions. At least one hemodynamic quantity characterizing functional severity of a renal stenosis region is calculated based on the simulated blood flow and pressure in the portion of the renal arteries and aorta.

42 Claims, 4 Drawing Sheets

(51) Int. Cl.
  *G01R 33/563* (2006.01)
  *A61B 5/055* (2006.01)
(52) U.S. Cl.
  CPC .... *A61B 2576/023* (2013.01); *G01R 33/5635* (2013.01); *G01R 33/56316* (2013.01)

(56) References Cited

U.S. PATENT DOCUMENTS

| | | | |
|---|---|---|---|
| 8,224,640 | B2 | 7/2012 | Sharma et al. |
| 8,315,812 | B2 | 11/2012 | Taylor |
| 8,386,188 | B2 | 2/2013 | Taylor et al. |
| 8,496,594 | B2 † | 7/2013 | Taylor |
| 2005/0156593 | A1* | 7/2005 | Assmann ............ A61B 5/0263 324/306 |
| 2010/0067760 | A1 | 3/2010 | Zhang et al. |
| 2011/0224542 | A1 | 9/2011 | Mittal et al. |
| 2012/0022843 | A1 | 1/2012 | Ionasec et al. |
| 2012/0041301 | A1 | 2/2012 | Redel |
| 2012/0041735 | A1 | 2/2012 | Taylor |
| 2012/0072190 | A1 | 3/2012 | Sharma et al. |
| 2012/0121151 | A1 | 5/2012 | Bernhardt et al. |
| 2012/0203530 | A1 | 8/2012 | Sharma et al. |
| 2013/0246034 | A1 | 9/2013 | Sharma et al. |
| 2014/0058715 | A1 | 2/2014 | Sharma et al. |
| 2015/0332015 | A1 † | 11/2015 | Taylor |

OTHER PUBLICATIONS de Bruyne, "Simultaneous Coronary Pressure and Flow Velocity Measurements in Humans," Circulation, vol. 94, pp. 1842-1849, 1996.

Anderson, "Coronary Artery Flow Velocity is Related to Lumen Area and Regional Left Ventricular Mass," Circulation, vol. 102, pp. 48-54, 2000.

Chamuleau, "Association between Coronary Lesion Severity and Distal Microvascular Resistance in Patients with Coronary Artery Disease," Am J Physiol Heart Circ Physiol, vol. 285, pp. H2194-H2200, 2003.

\* cited by examiner
† cited by third party

METHOD AND SYSTEM FOR FUNCTIONAL ASSESSMENT OF RENAL ARTERY STENOSIS FROM MEDICAL IMAGES

This application claims the benefit of U.S. Provisional Application No. 61/873,399, filed Sep. 4, 2013, and U.S. Provisional Application No. 61/891,920, filed Oct. 17, 2013, the disclosures of which are herein incorporated by reference in their entirety.

BACKGROUND OF THE INVENTION

The present invention relates to functional assessment of renal artery stenosis, and more particularly, to non-invasive functional assessment of renal artery stenosis from medical image data and blood flow simulations.

Renal artery stenosis (RAS) is the narrowing of the renal artery. RAS can impede blood flow to the target kidney and may result in hypertension, atrophy of the affected kidney, and ultimately renal failure if not treated. Medical image based anatomical assessment of RAS is routinely done in clinical practice. A number of imaging modalities, including magnetic resonance imaging (MRI), computed tomography (CT), x-ray angiography, and ultrasound, are used for this purpose, and each of these imaging modalities provides some estimate of the anatomical narrowing of the renal artery due to the blockage. Nevertheless, the true hemodynamic significance of RAS cannot typically be assessed by merely estimating the anatomical narrowing of the renal artery. The hemodynamic significance of RAS can be determined using an invasive catheterization procedure to insert a pressure wire to measure the pressure drop across the stenosis. However, this procedure is not widely used for RAS, mostly due to the invasive nature of the procedure.

In recent years, large multi-center trials have demonstrated the drawbacks of using anatomical severity of the RAS of as the criterion for stenting. Studies have shown that the functional assessment of RAS is important for identifying patients who will benefit from stenting.

BRIEF SUMMARY OF THE INVENTION

The present invention provides a method and system for non-invasive functional assessment of renal artery stenosis. Embodiments of the present invention provide a non-invasive method for computing the functional and anatomical severity of a renal artery stenosis by using medical image data and flow simulations.

In one embodiment of the present invention, a patient-specific anatomical model of at least a portion of the renal arteries and aorta is generated from medical image data of a patient. Patient-specific boundary conditions of a computational model of blood flow in the portion of the renal arteries and aorta are estimated based on the patient-specific anatomical model. Blood flow and pressure are simulated in the portion of the renal arteries and aorta using the computational model based on the patient-specific boundary conditions. At least one hemodynamic quantity characterizing functional severity of a renal stenosis region is calculated based on the simulated blood flow and pressure in the portion of the renal arteries and aorta.

These and other advantages of the invention will be apparent to those of ordinary skill in the art by reference to the following detailed description and the accompanying drawings.

DETAILED DESCRIPTION

The present invention relates to a method and system for non-invasive functional assessment of renal artery stenosis using medical image data and blood flow simulations. Embodiments of the present invention are described herein to give a visual understanding of the methods for simulating blood flow and assessing renal artery stenosis. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
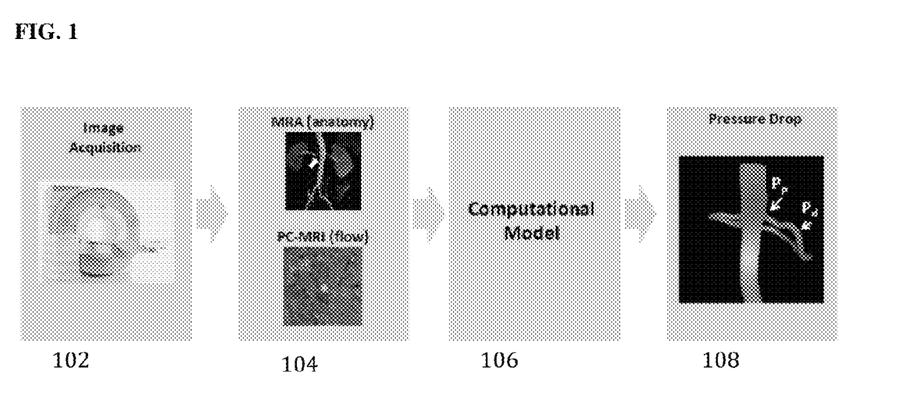
FIG. 1 illustrates a framework for non-invasive functional assessment of renal artery stenosis according to an embodiment of the present invention.

FIG. 1 illustrates a framework for non-invasive functional assessment of renal artery stenosis according to an embodiment of the present invention. In the embodiment of FIG. 1, image acquisition 102 results medical image data 104 including magnetic resonance angiography (MRA) images used to extract the renal anatomy of the patient and phase contrast MRI (PCMRI) images used to obtained flow measurements. The computational model 106 is based on a numerical model for blood flow computation which involves solving the Navier-Stokes equations describing the physics of fluid flow. The boundary conditions of the computational model 106 are determined from flow measurements obtained from the PCMRI images. In the absence of flow measurements, other physiologically apt boundary conditions, such as Windkessel, structured tree, etc., may also be used to model the effect of blood flow in the downstream and upstream parts of the circulatory system. In addition, the image acquisition 102 may be performed at different physiological states of the patient, such as at rest, during induced hyperemia, during exercise, etc., to capture the relevant anatomical and functional measurements for the computational model 106. The blood flow simulations performed by the computational model are used to compute a pressure drop 108 across the renal artery stenosis. In particular, the pressure drop 108 is computed from the simulated proximal pressure ($P_p$) and distal pressure ($P_d$) to the renal artery stenosis.

Figure 2:
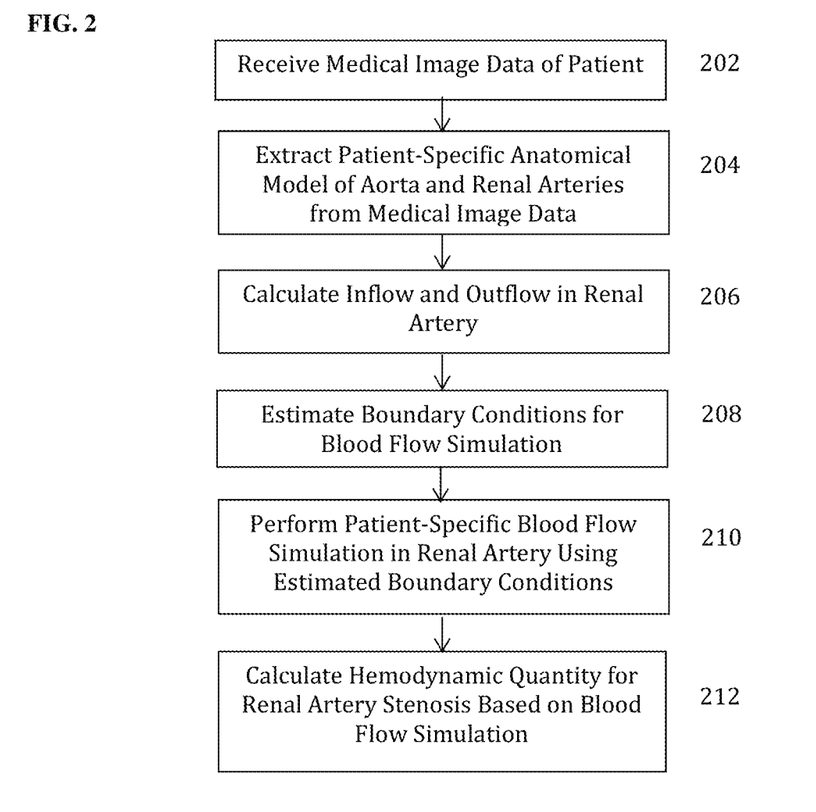
FIG. 2 illustrates a method for non-invasive functional assessment of renal artery stenosis according to an embodiment of the present invention.

FIG. 2 illustrates a method for non-invasive functional assessment of renal artery stenosis according to an embodiment of the present invention. Referring to FIG. 2, at step 202, medical image data of a patient is received. Medical image data from one or multiple imaging modalities can be received. For example, the medical image data can include, computed tomography (CT), Dyna CT, magnetic resonance imaging (MRI), Angiography, Ultrasound, Single Photon Emission computed Tomography (SPECT), and any other type of medical imaging modality. The medical image data can be 2D, 3D or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient. In an advantageous embodiment, the medical image data can include anatomical image data and flow image data. For example, the anatomical image data can MRA images or CT images, and the flow image data can be PCMRI images or Doppler ultrasound images, but the present invention is not limited thereto. In addition to the medical image data, other non-invasive clinical measurements, such as the patient's heart rate and systolic and diastolic blood pressure may also be acquired.

A clinician may be provided with an option of identifying a stenosis of interest in the renal arteries by interactively viewing them on the images. This step can also be performed on the anatomical model that is extracted from the image data (step 204). Alternatively, one or more renal artery stenoses may be automatically detected in the image data using an algorithm for automatic detection of renal artery stenosis. For example, a method similar to the method for automatic detection of coronary artery stenosis described in United States Published Patent Application No. 2011/0224542, which is incorporated herein by reference, may be used to automatically detect renal artery stenosis.

In a possible embodiment, the medical image data may be acquired at a plurality of different physiological states of the patient, such as at rest, during induced hyperemia, during exercise, etc., to capture the relevant anatomical and functional measurements to compute boundary conditions for blood flow simulations at different physiological states. In another possible embodiment, the medical image data can be acquired at a single physiological state (e.g., rest) and boundary conditions for other physiological states (e.g., hyperemia) can be derived from the medical image data and other non-invasive clinical measurements acquired at that state.

At step 204, a patient-specific anatomical model of the renal arteries and aorta is extracted from the medical image data. The patient-specific anatomical model is extracted using image segmentation algorithms, such as intensity thresholding, region-growing, machine-learning based techniques, and vessel tracking algorithms. The anatomical model can be a 3D surface or volume mesh, or a centerline tree tagged with vessel radius values. In the case in which medical image data is acquired at different physiological states (e.g., rest, hyperemia, etc.), a respective patient-specific anatomical model of the renal arteries and aorta can be extracted from the medical image data acquired at each physiological states.

In a possible embodiment, the renal arteries can be segmented in 3D medical image data using an automated renal artery centerline extraction algorithm. For example, a centerline extraction method similar to the method described in United States Published Patent Application No. 2010/0067760, which is incorporated herein by reference, can be applied to the renal arteries to extract centerlines of the renal arteries. Once the renal artery centerlines are extracted, cross-section contours can be generated at each point of the centerlines. The cross-section contour at each centerline point gives a corresponding cross-section area measurement at that point in the coronary artery. A geometric surface model may then be generated for the segmented renal arteries. In addition to the renal arteries, the patient-specific anatomical model can include at least a proximal portion of the aorta. A detailed 3D model of each renal artery stenosis is also extracted using similar algorithms, which includes the quantification of the proximal vessel diameter and area, distal vessel diameter and area, minimal lumen diameter and area, and length of stenosis.

The above described anatomical modeling tasks can be performed automatically or can be user-driven, thereby allowing the user (clinician) to interactively make changes to the anatomical models to analyze the effects of such changes on the subsequent blood flow simulations and computation of hemodynamic parameters.

Figure 3:
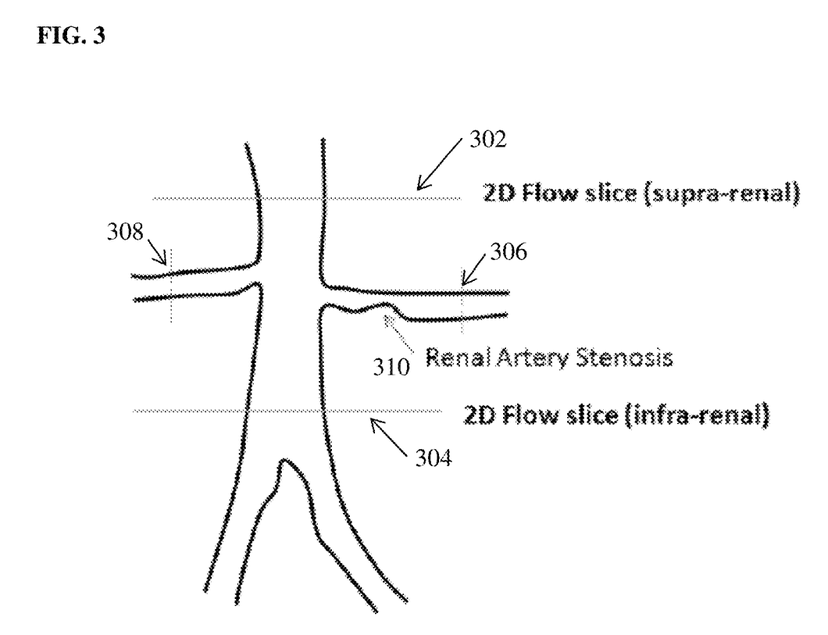
FIG. 3 illustrates exemplary 2D flow slices used to quantify the inflow and outflow to a renal artery stenosis.

At step 206, inflow and outflow are calculated in the renal artery. This step is performed when flow image data, such as PCMRI images of the patient, is available. The flow image data may be 2D, 3D, or 4D flow image data. In order to quantify the flow in the renal arteries the patient-specific anatomical model of the renal arteries and aorta is used to mask the flow image data in order to obtain the flow information in the lumen. According to an advantageous implementation, the inflow and outflow in a target lumen is quantified by computing average values, such as time-varying flow rates, in 2D slices of the flow image data corresponding to specific locations on the patient-specific anatomical model. FIG. 3 illustrates exemplary 2D flow slices used to quantify the inflow and outflow to a renal artery stenosis. As shown in FIG. 3, flow rates measured in four 2D flow slices 302, 304, 306, and 308 are used to quantify the inflow and outflow to the renal artery stenosis 310. Slice 302 is a supra-renal cross-section of the aorta and slice 304 is an infra-renal cross-section of the aorta. Slice 306 corresponds to a cross-section of the target renal artery (i.e., the renal artery in which the renal artery stenosis 310 is located) distal to the renal artery stenosis. Slice 308 corresponds to a cross-section of the other renal artery. The 2D flow slices can be 2D PCMRI images acquired at each of the specified locations. The flow measurements in these slices 302, 304, 308, and 310 can be used to establish inflow and outflow boundary conditions for the blood flow simulation.

Returning to FIG. 2, at step 208, patient-specific boundary conditions for the blood flow simulation are estimated. In one possible embodiment, the boundary conditions at the inlets and outlets of the computation domain are directly specified from the flow measurements obtained in step 206. For example, when the flow measurements are obtained using the 2D flow slices shown in FIG. 3, the inlet and outlets of the computational domain are defined at the locations of the 2D flow slices. The flow measured in slice 302 is used as the boundary condition for the inlet of the computational domain and the flow measured in slices 304, 306, and 308 is used as the boundary condition are respective outlets of the computational domain.

In another embodiment of the present invention, the boundary conditions are estimated based on the patient-specific anatomical model and patient-specific clinical measurements using physiological assumptions. This embodiment may be utilized when flow image data of the patient is not available. For example, boundary conditions may be estimated using Windkessel elements or structured tree type conditions to model the distal vasculature. These conditions can be personalized based on anatomical measurements, such as vessel radii, for an individual patient. Techniques similar to those described in United States Published Patent Application No. 2014/0058715, United States Published Patent Application No. 2013/0246034, and International Publication No. WO 2013/138428 A1, the disclosures of which are incorporated by reference in their entirety, can be used for estimating patient-specific boundary conditions using anatomical measurements and/or clinical measurements of a patient.

The hemodynamic quantities of interest for function assessment of renal artery stenosis, such as FFR, are based on average values of flow or pressure over the cardiac cycle. For an efficient clinical workflow for evaluation such hemodynamic quantities via simulations, a balance between model complexity and computation time, without compromising on the accuracy of the results is desirable. In an advantageous embodiment of the present invention, reduced-order models are used for the patient-specific blood flow simulation, which enables the assessment of the functional significance of a renal artery stenosis. The reduced-order models provide accurate estimates of flow and pressure distribution in the renal arteries, and are computationally efficient, thus enabling a seamless integration with the clinical workflow. Although the reduced order model is described herein for blood flow simulation in the renal arteries, the present invention is not limited thereto, and a full-scale model or a multi-scale model of the patient's circulatory system can be used as well.

In a possible embodiment of the present invention, a heart model can be coupled at the root of the aorta. The heart model may be implemented as a full 3D heart model or may be implemented as a lumped model parameterized through patient-specific data. The aorta and the large arteries (e.g., the left coronary artery (LCA), right coronary artery (RCA), etc.) can be represented as 1D blood flow models since these 1D blood flow models produce reliable results in terms of pressure and flow rate values and take into account wave propagation phenomena. All microvascular beds can be simulated through lumped parameter models which account for the resistance applied to the blood flow and for the compliance of the distal vessels. For the renal arteries, the flow in can be computed through 1D models. The stenosis segment (i.e., area in the renal arteries where stenosis or narrowing is detected) cannot be simulated using the 1D blood flow models since there is a high variation in cross-sectional area and the shape of the stenosis influences the blood flow behavior and especially the trans-stenotic pressure drop which plays a major role in the assessment of the functional importance of such a stenosis.

Reduced-Order Model of Circulation

The large arteries supplied by the aorta (e.g. coronary arteries, renal arteries, etc.) are modeled as axi-symmetric 1-D vessel segments, where the blood-flow satisfies the following properties: conservation of mass, conservation of momentum, and a state equation for wall deformation. The vessel wall can modeled as a purely elastic or visco-elastic. The inlet boundary condition can be prescribed through an implicit coupling with the heart model, or through measured flow data. The outlet boundary condition is given by the implicit coupling with the models of the vascular beds distal to the arteries, while the junctions (bifurcations) are solved by considering the continuity of total pressure and flow. Additionally, the following loss coefficients may be introduced which account for the energy loss at the junctions, which depend on the angles between the vessel segments:

$$\frac{\partial A(t)}{\partial t} + \frac{\partial q(t)}{\partial x} = 0 \tag{1}$$

$$\frac{\partial q(t)}{\partial t} + \frac{\partial}{\partial t}\left(\alpha \frac{q^2(t)}{A(t)}\right) + \frac{A(t)}{\rho}\frac{\partial p(t)}{\partial x} = K_R \frac{q(t)}{A(t)} \tag{2}$$

$$p(t) = \frac{4}{3}\frac{Eh}{r_0}\left(1 - \sqrt{\frac{A_0}{A(t)}}\right), \tag{3}$$

where q is the flow rate, A is the cross-sectional area, p is the pressure, $\alpha$ is the momentum-flux correction coefficient, $K_R$ is a friction parameters, $\rho$ is the density, E is the Young modulus, h is the wall thickness and $r_0$ is the initial radius. The wall properties may be determined through an empirical relationship fit to the measured data in the extracted patient-specific anatomical model or based on patient-specific estimations of the wall compliance. Other alternative formulations of the quasi-1-D flow equations can also be used, modeling the effects of visco-elasticity, non-Newtonian behavior, etc.

Stenosis Pressure Drop Model

The above quasi 1-D equations (Equations 1-3) are derived by considering a series of simplifying assumptions which all hold well for normal, healthy vessels. One of the assumptions is that the axial velocity is dominant and the radial components are negligible. This assumption no longer holds in case of sudden changes in lumen diameter, e.g. for a stenosis, and the radial components can no longer be excluded. Hence, the quasi 1-D equations do not correctly capture the pressure drop across the stenosis.

In terms of previous research activities, much attention has been directed towards the local velocity fields, but for the hemodynamic quantities, such as FFR, assessment only the trans-stenotic pressure drop is important. In an advantageous implementation, a semi-empirical reduced-order stenosis pressure-drop model can be included in the 1-D blood flow models, which obtain accurate results as compared to full scale models. For example, in the model below, the pressure drop is expressed as a sum of three terms (viscous term, turbulent or Bernoulli term, and inertance term):

$$\Delta P_s = \frac{\mu K_v}{2\pi r_0^3}q + \frac{\rho K_t}{2A_0^2}\left(\frac{A_0}{A_s} - 1\right)^2 |q|q + \frac{\rho K_u L_s}{A_0}\frac{\partial q}{\partial t}, \tag{4}$$

where $\mu$ is the blood viscosity, $L_s$ is the stenosis length, $K_v$, $K_t$ and $K_u$ are the viscous, turbulent, and inertance coefficients, respectively (all the quantities indexed with 0 refer to the normal dimensions while the quantities indexed with s refer to the stenosed values). In an advantageous embodiment, such a reduced-order stenosis pressure-drop model for a renal artery stenosis segment is coupled with the 1D renal artery model to compute the physiological pressure drop across the stenosis. In a possible implementation, this pressure drop can be calculated at both during rest state and at maximal hyperemia. It is to be understood that the present invention is not limited to the semi-empirical stenosis pressure-drop model of Equation (4), and other such models of the stenosis, with multiple pressure drop factors, may be used alternatively. Additionally, in an alternative implementation, a full-order 3D model of each renal artery stenosis may be coupled with the rest of the renal artery to simulate the pressure drop across the renal artery stenosis. In this case, the patient-specific 3D geometric model of the renal artery stenosis extracted from the medical image data (e.g., CTA data) is used in conjunction with stenosis geometry measures to personalize the stenosis model for the individual patient.

Regarding coupling of the reduced-order or full-order renal artery stenosis model to the rest of the renal artery model, in a first possible implementation, the momentum equation is adapted and the additional pressure drop determined by the turbulent term is included on the right hand side of the equation as an additional loss term. In a second possible implementation, the regular momentum equation is disregarded completely and replaced by Equation (2). The segments treated as stenosis segments are coupled to the regular segments of the renal artery by considering continuity of total pressure and flow rate.

Patient-Specific Modeling of Microvascular Bed Boundary Conditions

An important aspect of the flow simulations is represented by the boundary conditions at the termination of the renal arteries (outflow boundary conditions). Generally, pressure, flow, or a relationship between flow and pressure may be imposed at the terminal sites of the renal arteries. If measured data, e.g. time-varying velocity, flow rate, or even pressure, are available, they can be readily applied. In the absence of such information (which is typically the case), embodiments of the present invention calculate special boundary conditions that model the behavior of the distal arterial segments. Hence, the microvascular beds are modeled through lumped or 0-D models: the systemic beds can represented by regular Windkessel elements containing varying number of elements (for example, between two and four elements), while renal microvessel beds may be modeled similarly.

The microvascular bed can be treated as a single unit, but it is also possible to utilize more specialized models which consider separately the contribution of the arterioles and capillaries.

Since the resistance values of the large vessels are very small compared to the resistances of the arterioles and capillaries, the overall pressure levels are almost solely determined by the microvascular beds. In the context of non-invasive hemodynamic evaluation (for example renal artery FFR), the microvascular beds in general, and the coronary beds in particular play another major role. Since FFR is based on values determined at hyperemia, in order to non-invasively determine the value of this diagnostic indicator, the blood flow simulation has to model the hyperemic state. In clinical practice, FFR is measured after the intravenous or intracoronary administration of a vasodilator.

The administration of hyperemia inducing drugs (adenosine, papaverine etc.) leads to a vasodilation effect of the microvascular beds, which represents an important decrease of the resistance values. The resistance values inside the systemic or lumped models (for the normal state) may be obtained from patient-specific measurements, from literature data, or from the non-linear relationship between resistances and lumen size. Compliances play a secondary role since they only influence the transient values and not the average pressures which are of interest for the evaluation of FFR. The hyperemic state is modeled through a corresponding decrease in the microvascular resistances, as caused by the administration of adenosine and leads to an increase of normal flow in healthy vessels.

The main parameters which have to be estimated are the mean arterial pressure (MAP) and the microvascular resistances. Since FFR uses only average measures of pressures (distal and proximal to the stenosis), compliances need not be estimated accurately because they only influence the waveform of pressure and flow, but not the average values, which are only determined by the resistances. MAP can be easily measured non-invasively and as stated previously is similar at both rest and hyperemia state. Microvascular resistances on the other hand are much lower at hyperemia in order to allow for an increased flow rate. To determine the resistance values at hyperemia, first, the rest resistances can be estimated and then the effect of the administration of a vasodilation drug can be estimated and the hyperemia resistances can be estimated.

According to an advantageous embodiment of the present invention, the calculation of patient-specific boundary conditions for the microvessel bed is implemented in two stages: in the first stage, the mean arterial pressure (MAP) and the microvascular resistance at each outlet of the patient-specific vessel tree during a simulated rest-state are estimated, and in the second stage, the microvascular resistances at hyperemia are estimated.

The mean arterial pressure (MAP) can be estimated based on the patient's heart rate, systolic blood pressure, diastolic blood pressure. In particular, the MAP is calculated as $$MAP = DBP + [\tfrac{1}{3} + (HR \cdot 0.0012)] \cdot (SBP - DBP), \quad (5)$$

where HR, SBP, and DBP denote the patient's heart rate, systolic blood pressure, diastolic blood pressure, respectively, which are measure non-invasively.

In order to distribute flow in different vessels, a morphometric relationship may be used. For example:

$$Q_{rest} = \sum_{i=1}^{n} k \cdot r_i^3 = \sum_{i=1}^{n} Q_i. \quad (6)$$

A terminal resistance for each vessel can then be calculated using the following relationship:

$$R_i = \frac{MAP}{Q_i}. \quad (7)$$

$Q_i$ is determined by:

$$\frac{Q_i}{Q_{rest}} = \frac{k \cdot r_i^3}{\sum_{j=1}^{n} k \cdot r_j^3} = \frac{r_i^3}{\sum_{j=1}^{n} r_j^3}, \quad (8)$$

and hence:

$$Q_i = \frac{Q_{rest} \cdot r_i^3}{\sum_{j=1}^{n} r_j^3}, \quad (9)$$

where $r_i$ is the terminal radius of a vessel (equal to half of the terminal diameter $d_i$) and n is a power coefficient. Thus, the terminal resistance at each vessel can be calculated as:

$$R_i = \frac{MAP}{Q_i} = \frac{MAP \cdot \sum_{j=1}^{n} r_j^3}{Q_{rest} \cdot r_i^3}. \quad (10)$$

The second stage of estimating the patient-specific microvessel bed boundary conditions calculates hyperemic-state microvascular resistances based on the rest-state microvascular resistances. The hyperemic state can be modeled by decreasing the microvascular resistances, which is caused by the administration of intracoronary adenosine. The boundary conditions of the rest-state and hyperemia-state microvascular resistances can be determined using a similar method to those described in United States Published Patent Application No. 2013/0243294, entitles "Method and System for Hemodynamic Assessment of Aortic Coarctation from Medical Image Data", and Itu et al., "Non-Invasive Hemodynamic Assessment of Aortic Coarctation: Validation with in vivo Measurements", *Ann Biomed Eng.* 2013 April; 41(4):669-8, the disclosures of which are incorporated herein by reference in their entirety According to an advantageous embodiment, to ensure that the computed flow quantities are in agreement with the measured data, an iterative optimization based approach can be used to tune the boundary conditions until the error is reduced below a threshold value. For example, an iterative optimization based approach may be used that is similar to the approach described in International Publication No. WO 2013/138428 A1, the disclosure of which is incorporated by reference.

Returning to FIG. 2, at step 210, patient-specific blood flow simulations are performed in the renal artery using the estimated boundary conditions. The blood flow simulations are performed by computing a numerical solution of the physical flow equations, such as Navier-Stokes equations, with the estimated boundary conditions. Depending on the model used, the flow equations may be 0D, 1D, 2D, or 3D in the spatial domain, and steady or unsteady in the time domain. Such blood flow simulations can be performed similar to the blood flow simulations described in United States Published Patent Application No. 2014/0058715, United States Published Patent Application No. 2013/0246034, U.S. Pat. No. 8,224,640, and International Publication No. WO 2013/138428 A1, the disclosures of which are incorporated by reference in their entirety. The blood flow simulations result in simulated blood flow and pressure throughout the computational domain, which provides a simulated pressure drop across the renal artery stenosis. According to an embodiment of the present invention, blood flow simulations can be performed for a plurality of physiological states of the patient, such as rest and maximal hyperemia.

Results of the blood flow simulations can be output, for example by displaying pressure maps and or velocity fields resulting from the blood flow simulations on a display device of a computer system.

At step 212, one or more hemodynamic quantity can be calculated for the renal artery stenosis based on the blood flow simulations. The computed flow values can be used to calculate other derived quantities, such as a trans-stenotic pressure gradient, flow reserves, energy loss, etc., which characterize the functional severity of the renal artery stenosis. These are then used in conjunction with the anatomical measurements of severity, such as radius reduction, minimal lumen diameter/area, etc., to provide a comprehensive assessment of the renal artery stenosis. It is to be understood that if there is more than one renal artery stenosis, respective hemodynamic quantities are calculated for each stenosis.

According to a possible implementation, fractional flow reserve (FFR) is calculated for the renal artery stenosis based on the blood flow simulations. Once the time-varying pressure and flow rates are computed from the blood flow simulations at maximal vasodilation (hyperemia), the FFR value is determined by simply taking the ratio of the mean pressure distal to the stenosis ($P_d$) with respect to the mean aortic pressure ($P_a$) during the cardiac cycle:

$$FFR = \frac{P_d}{P_a}. \tag{26}$$

This calculation can be performed automatically for any renal artery stenosis specified during the anatomic modeling step. Additionally, the user can also specify any location in the renal artery during a post-processing step, and the corresponding FFR value will then be computed as described above.

The method of FIG. 1 illustrates one embodiment for non-invasive assessment of renal artery stenosis using medical image data. In another embodiment of the present invention, medical images with flow measurements (e.g., PC-MRI, Ultrasound Doppler) may be used directly (and not just as boundary conditions) to calculate the pressure drop in the renal arteries. For example, if 4D flow volume data is acquired, then a pressure-Poisson equation or Bernoulli's equation may be used to estimate pressure-drop in a certain region of the volume without explicitly doing a Computational Fluid Dynamics simulation (which requires a 3D mesh and boundary condition setup). It should be noted that such a step does not require an anatomical model of the renal arteries to be extracted. All existing such methods require an intermediate step of obtaining a geometric model of the organ or vasculature by segmenting the medical image. This step is typically effort-intensive and also the source of considerable inter-user variability.

In another embodiment, the computation of hemodynamic quantity (for example pressure) may be performed directly on the anatomical medical image, without extracting organ specific geometric information. This is in contrast to the case where a flow image is used (as described in the previous paragraph). This may be done by treating the image grey values (or transformations of the image voxels) as a porosity map, and solving a porous flow problem (for example: Darcy's law) directly on the image voxels to compute flow in entire image. Such methods have been used for image segmentation, but not for computing hemodynamic quantities from images.

In another embodiment, features may be extracted from a medical image (anatomic and/or functional), which may then be used to compute hemodynamic quantity (such as pressure or flow) without doing a CFD-based flow computation. For such an approach, a machine learning approach may be used to learn the relationship between the features derived from the medical images and the hemodynamic quantity of interest. For example, geometrical features derived from the image of the renal artery (and the stenosis) may be used in a first step to learn a mapping from features to pressure-drop. Here the ground-truth (pressure-drop in this case) may either be invasively measured pressure or a simulated quantity on patient data or phantom data).

Figure 4:
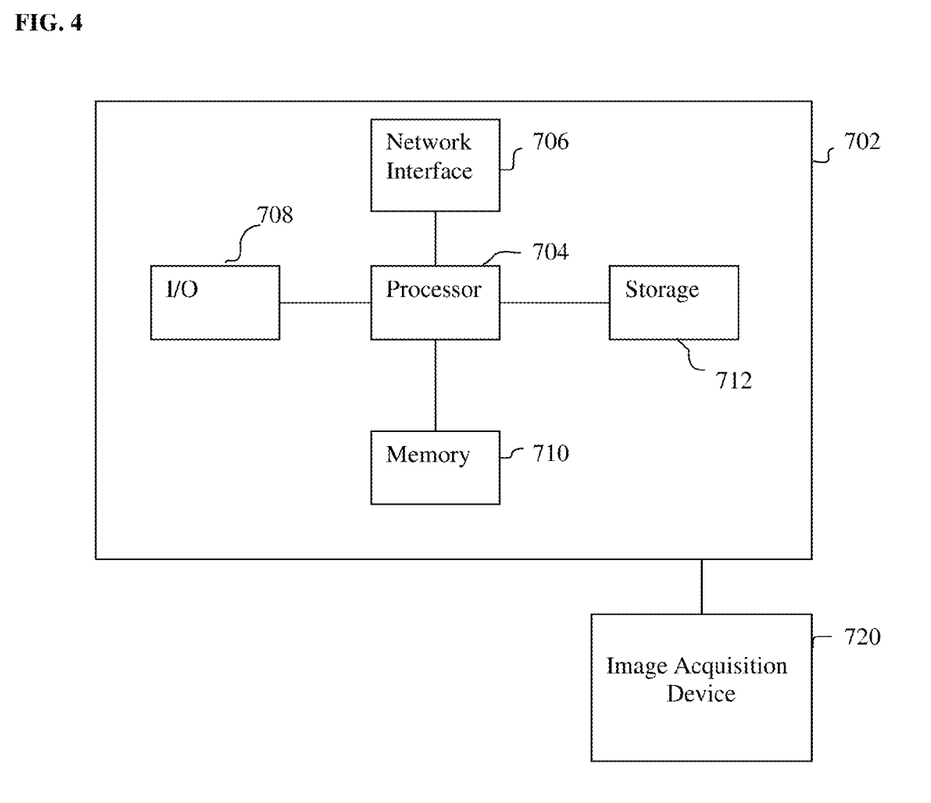
FIG. 4 is a high-level block diagram of a computer capable of implementing the present invention.

The above-described methods for non-invasive assessment of renal artery stenosis may be implemented on a computer using well-known computer processors, memory units, storage devices, computer software, and other components. A high-level block diagram of such a computer is illustrated in FIG. 4. Computer 402 contains a processor 404, which controls the overall operation of the computer 402 by executing computer program instructions which define such operation. The computer program instructions may be stored in a storage device 412 (e.g., magnetic disk) and loaded into memory 410 when execution of the computer program instructions is desired. Thus, the steps of the methods of FIGS. 1 and 2 may be defined by the computer program instructions stored in the memory 410 and/or storage 412 and controlled by the processor 404 executing the computer program instructions. An image acquisition device 420, such as a CT scanning device, MR scanning device, Ultrasound device, etc., can be connected to the computer 402 to input image data to the computer 402. It is possible to implement the image acquisition device 420 and the computer 402 as one device. It is also possible that the image acquisition device 420 and the computer 402 communicate wirelessly through a network. The computer 402 also includes one or more network interfaces 406 for communicating with other devices via a network. The computer 402 also includes other input/output devices 408 that enable user interaction with the computer 402 (e.g., display, keyboard, mouse, speakers, buttons, etc.). Such input/output devices 408 may be used in conjunction with a set of computer programs as an annotation tool to annotate volumes received from the image acquisition device 420. One skilled in the art will recognize that an implementation of an actual computer could contain other components as well, and that FIG. 4 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for assessment of renal artery stenosis, comprising:
   generating a patient-specific anatomical model of at least a portion of the renal arteries and aorta from medical image data of a patient;
   estimating patient-specific boundary conditions of a computational model of blood flow in the portion of the renal arteries and aorta based on the patient-specific anatomical model;
   simulating blood flow and pressure in the portion of the renal arteries and aorta using the computational model based on the patient-specific boundary conditions; and
   calculating at least one hemodynamic quantity characterizing functional severity of a renal stenosis region based on the simulated blood flow and pressure in the portion of the renal arteries and aorta,
   wherein the computational model comprises a reduced order stenosis pressure-drop model representing the renal stenosis region coupled to a one-dimensional computational model representing a renal artery and the reduced order stenosis pressure-drop model calculates a pressure drop across the renal stenosis region as a sum of a viscous term, a turbulent term, and an inertance term.

2. The method of claim 1, further comprising:
   quantifying at least one inflow and at least one outflow to the portion of the renal arteries and aorta.

3. The method of claim 2, wherein estimating patient-specific boundary conditions of a computational model of blood flow in the portion of the renal arteries and aorta based on the patient-specific anatomical model comprises:
   determining inlet and outlet boundary conditions using the quantified at least one inflow and at least one outflow to the portion of the renal arteries and aorta.

4. The method of claim 2, wherein quantifying at least one inflow and at least one outflow to the portion of the renal arteries and aorta comprises:
   measuring flow rates in each of a plurality of 2D flow slices corresponding to inlet and outlet positions of the portion of the renal arteries and aorta.

5. The method of claim 4, wherein the plurality of 2D flow slices comprise a first 2D flow slice that is a supra-renal cross-section of the aorta, a second 2D flow slice that is a infra-renal cross-section of the aorta, a third 2D flow slice that is a cross-section of a target renal artery distal to the renal stenosis region, and a fourth 2D flow slice that is a cross-section of a non-target renal artery.

6. The method of claim 4, wherein each of the plurality of 2D flow slices is a 2D phase-contrast magnetic resonance imaging (PCMRI) image.

7. The method of claim 2, wherein quantifying at least one inflow and at least one outflow to the portion of the renal arteries and aorta comprises:
   masking a flow image of the patient using the patient-specific anatomical model to obtain flow information in a lumen of the portion of the renal arteries and aorta.

8. The method of claim 1, wherein estimating patient-specific boundary conditions of a computational model of blood flow in the portion of the renal arteries and aorta based on the patient-specific anatomical model comprises:
   estimating patient-specific boundary conditions of the computational model for a plurality of physiological states of the patient.

9. The method of claim 8, wherein estimating patient-specific boundary conditions of the computational model for a plurality of physiological states of the patient comprises:
   estimating the patient-specific boundary conditions for each of the plurality of physiological states based on a respective patient-specific anatomic model extracted from medical image data acquired at each of the plurality of physiological states.

10. The method of claim 8, wherein estimating patient-specific boundary conditions of the computational model for a plurality of physiological states of the patient comprises:
    estimating patient-specific boundary conditions for a rest state based on the patient-specific anatomical model extracted from medical image data acquired at a rest state; and
    estimating patient-specific boundary conditions for a hyperemic state based on the estimated patient-specific boundary conditions for the rest state.

11. The method of claim 1, wherein calculating at least one hemodynamic quantity characterizing functional severity of a renal stenosis region based on the simulated blood flow and pressure in the portion of the renal arteries and aorta comprises:
    calculating a pressure drop across the renal stenosis region based on the simulated blood flow and pressure.

12. The method of claim 1, wherein calculating at least one hemodynamic quantity characterizing functional severity of a renal stenosis region based on the simulated blood flow and pressure in the portion of the renal arteries and aorta comprises:
  calculating fractional flow reserve (FFR) for the renal stenosis region based on the simulated blood flow and pressure.

13. The method of claim 1, wherein computational model comprises one-dimensional computational models representing the renal arteries and aorta of the patient.

14. The method of claim 1, wherein the computational model comprises lumped models representing microvascular beds, each coupled to a termination of a one-dimensional computational model representing a respective renal artery.

15. An apparatus for assessment of renal artery stenosis, comprising:
  a processor; and
  a memory storing computer program instructions, which when executed by the processor cause the processor to perform operations comprising:
    generating a patient-specific anatomical model of at least a portion of the renal arteries and aorta from medical image data of a patient;
    estimating patient-specific boundary conditions of a computational model of blood flow in the portion of the renal arteries and aorta based on the patient-specific anatomical model;
    simulating blood flow and pressure in the portion of the renal arteries and aorta using the computational model based on the patient-specific boundary conditions; and
    calculating at least one hemodynamic quantity characterizing functional severity of a renal stenosis region based on the simulated blood flow and pressure in the portion of the renal arteries and aorta,
  wherein the computational model comprises a reduced order stenosis pressure-drop model representing the renal stenosis region coupled to a one-dimensional computational model representing a renal artery and the reduced order stenosis pressure-drop model calculates a pressure drop across the renal stenosis region as a sum of a viscous term, a turbulent term, and an inertance term.

16. The apparatus of claim 15, wherein the operations further comprise:
  quantifying at least one inflow and at least one outflow to the portion of the renal arteries and aorta.

17. The apparatus of claim 16, wherein estimating patient-specific boundary conditions of a computational model of blood flow in the portion of the renal arteries and aorta based on the patient-specific anatomical model comprises:
  determining inlet and outlet boundary conditions using the quantified at least one inflow and at least one outflow to the portion of the renal arteries and aorta.

18. The apparatus of claim 16, wherein quantifying at least one inflow and at least one outflow to the portion of the renal arteries and aorta comprises:
  measuring flow rates in each of a plurality of 2D flow slices corresponding to inlet and outlet positions of the portion of the renal arteries and aorta.

19. The apparatus of claim 18, wherein the plurality of 2D flow slices comprise a first 2D flow slice that is a supra-renal cross-section of the aorta, a second 2D flow slice that is a infra-renal cross-section of the aorta, a third 2D flow slice that is a cross-section of a target renal artery distal to the renal stenosis region, and a fourth 2D flow slice that is a cross-section of a non-target renal artery.

20. The apparatus of claim 18, wherein each of the plurality of 2D flow slices is a 2D phase-contrast magnetic resonance imaging (PCMRI) image.

21. The apparatus of claim 16, wherein quantifying at least one inflow and at least one outflow to the portion of the renal arteries and aorta comprises:
  masking a flow image of the patient using the patient-specific anatomical model to obtain flow information in a lumen of the portion of the renal arteries and aorta.

22. The apparatus of claim 15, wherein estimating patient-specific boundary conditions of a computational model of blood flow in the portion of the renal arteries and aorta based on the patient-specific anatomical model comprises:
  estimating patient-specific boundary conditions of the computational model for a plurality of physiological states of the patient.

23. The apparatus of claim 22, wherein estimating patient-specific boundary conditions of the computational model for a plurality of physiological states of the patient comprises:
  estimating the patient-specific boundary conditions for each of the plurality of physiological states based on a respective patient-specific anatomic model extracted from medical image data acquired at each of the plurality of physiological states.

24. The apparatus of claim 22, wherein estimating patient-specific boundary conditions of the computational model for a plurality of physiological states of the patient comprises:
  estimating patient-specific boundary conditions for a rest state based on the patient-specific anatomical model extracted from medical image data acquired at a rest state; and
  estimating patient-specific boundary conditions for a hyperemic state based on the estimated patient-specific boundary conditions for the rest state.

25. The apparatus of claim 15, wherein the means for calculating at least one hemodynamic quantity characterizing functional severity of a renal stenosis region based on the simulated blood flow and pressure in the portion of the renal arteries and aorta comprises:
  calculating a pressure drop across the renal stenosis region based on the simulated blood flow and pressure.

26. The apparatus of claim 15, wherein calculating at least one hemodynamic quantity characterizing functional severity of a renal stenosis region based on the simulated blood flow and pressure in the portion of the renal arteries and aorta comprises:
  calculating fractional flow reserve (FFR) for the renal stenosis region based on the simulated blood flow and pressure.

27. The apparatus of claim 15, wherein computational model comprises one-dimensional computational models representing the renal arteries and aorta of the patient.

28. The apparatus of claim 15, wherein the computational model comprises lumped models representing microvascular beds, each coupled to a termination of a one-dimensional computational model representing a respective renal artery.

29. A non-transitory computer readable medium storing computer program instructions for assessment of renal artery stenosis, the computer program instruction when executed by a processor cause the processor to perform operations comprising:
  generating a patient-specific anatomical model of at least a portion of the renal arteries and aorta from medical image data of a patient;

estimating patient-specific boundary conditions of a computational model of blood flow in the portion of the renal arteries and aorta based on the patient-specific anatomical model;
simulating blood flow and pressure in the portion of the renal arteries and aorta using the computational model based on the patient-specific boundary conditions; and
calculating at least one hemodynamic quantity characterizing functional severity of a renal stenosis region based on the simulated blood flow and pressure in the portion of the renal arteries and aorta,
wherein the computational model comprises a reduced order stenosis pressure-drop model representing the renal stenosis region coupled to a one-dimensional computational model representing a renal artery and the reduced order stenosis pressure-drop model calculates a pressure drop across the renal stenosis region as a sum of a viscous term, a turbulent term, and an inertance term.

30. The non-transitory computer readable medium of claim 29, wherein the operations further comprise:
quantifying at least one inflow and at least one outflow to the portion of the renal arteries and aorta.

31. The non-transitory computer readable medium of claim 30, wherein estimating patient-specific boundary conditions of a computational model of blood flow in the portion of the renal arteries and aorta based on the patient-specific anatomical model comprises:
determining inlet and outlet boundary conditions using the quantified at least one inflow and at least one outflow to the portion of the renal arteries and aorta.

32. The non-transitory computer readable medium of claim 30, wherein quantifying at least one inflow and at least one outflow to the portion of the renal arteries and aorta comprises:
measuring flow rates in each of a plurality of 2D flow slices corresponding to inlet and outlet positions of the portion of the renal arteries and aorta.

33. The non-transitory computer readable medium of claim 32, wherein the plurality of 2D flow slices comprise a first 2D flow slice that is a supra-renal cross-section of the aorta, a second 2D flow slice that is a infra-renal cross-section of the aorta, a third 2D flow slice that is a cross-section of a target renal artery distal to the renal stenosis region, and a fourth 2D flow slice that is a cross-section of a non-target renal artery.

34. The non-transitory computer readable medium of claim 32, wherein each of the plurality of 2D flow slices is a 2D phase-contrast magnetic resonance imaging (PCMRI) image.

35. The non-transitory computer readable medium of claim 30, wherein quantifying at least one inflow and at least one outflow to the portion of the renal arteries and aorta comprises:
masking a flow image of the patient using the patient-specific anatomical model to obtain flow information in a lumen of the portion of the renal arteries and aorta.

36. The non-transitory computer readable medium of claim 29, wherein estimating patient-specific boundary conditions of a computational model of blood flow in the portion of the renal arteries and aorta based on the patient-specific anatomical model comprises:
estimating patient-specific boundary conditions of the computational model for a plurality of physiological states of the patient.

37. The non-transitory computer readable medium of claim 36, wherein estimating patient-specific boundary conditions of the computational model for a plurality of physiological states of the patient comprises:
estimating the patient-specific boundary conditions for each of the plurality of physiological states based on a respective patient-specific anatomic model extracted from medical image data acquired at each of the plurality of physiological states.

38. The non-transitory computer readable medium of claim 36, wherein estimating patient-specific boundary conditions of the computational model for a plurality of physiological states of the patient comprises:
estimating patient-specific boundary conditions for a rest state based on the patient-specific anatomical model extracted from medical image data acquired at a rest state; and
estimating patient-specific boundary conditions for a hyperemic state based on the estimated patient-specific boundary conditions for the rest state.

39. The non-transitory computer readable medium of claim 29, wherein calculating at least one hemodynamic quantity characterizing functional severity of a renal stenosis region based on the simulated blood flow and pressure in the portion of the renal arteries and aorta comprises:
calculating a pressure drop across the renal stenosis region based on the simulated blood flow and pressure.

40. The non-transitory computer readable medium of claim 29, wherein calculating at least one hemodynamic quantity characterizing functional severity of a renal stenosis region based on the simulated blood flow and pressure in the portion of the renal arteries and aorta comprises:
calculating fractional flow reserve (FFR) for the renal stenosis region based on the simulated blood flow and pressure.

41. The non-transitory computer readable medium of claim 29, wherein computational model comprises one-dimensional computational models representing the renal arteries and aorta of the patient.

42. The non-transitory computer readable medium of claim 29, wherein the computational model comprises lumped models representing microvascular beds, each coupled to a termination of a one-dimensional computational model representing a respective renal artery.

* * * * *